US010973627B2

(12) United States Patent
Polak (10) Patent No.: US 10,973,627 B2
(45) Date of Patent: Apr. 13, 2021

(54) APPARATUS FOR TREATMENT OF MENIÈRE'S DISEASE

(71) Applicant: MED-EL Elektromedizinische Geraete GmbH, Innsbruck (AT)

(72) Inventor: Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 119 days.

(21) Appl. No.: 15/737,367

(22) PCT Filed: Jun. 15, 2016

(86) PCT No.: PCT/US2016/037488
§ 371 (c)(1),
(2) Date: Dec. 18, 2017

(87) PCT Pub. No.: WO2016/205272
PCT Pub. Date: Dec. 22, 2016

(65) Prior Publication Data
US 2018/0161154 A1   Jun. 14, 2018

Related U.S. Application Data

(60) Provisional application No. 62/181,315, filed on Jun. 18, 2015.

(51) Int. Cl.
*A61F 2/18* (2006.01)
*A61N 1/05* (2006.01)
*A61F 11/00* (2006.01)

(52) U.S. Cl.
CPC ............... *A61F 2/18* (2013.01); *A61F 11/00* (2013.01); *A61N 1/0541* (2013.01); *A61F 2002/183* (2013.01)

(58) Field of Classification Search
CPC .............. A61N 1/0541; A61N 1/36036; A61N 1/36038; A61N 1/36039; A61F 2/18; A61F 11/00; A61F 11/002; A61F 2002/183
See application file for complete search history.

(56) References Cited

U.S. PATENT DOCUMENTS

| 4,757,807 A | 7/1988 | Densert et al. |
| 5,024,612 A | 6/1991 | van den Honert et al. |
(Continued)

FOREIGN PATENT DOCUMENTS

WO   WO 2005/072793 A1   8/2005

OTHER PUBLICATIONS

International Searching, International Search Report—International Application No. PCT/US16/37488, dated Sep. 9, 2016 together with the Written Opinion of the International Searching Authority, 15 pages.
(Continued)

*Primary Examiner* — George R Evanisko
(74) *Attorney, Agent, or Firm* — Sunstein LLP (57) ABSTRACT

An inner ear fluid circulation system includes an implantable circulation pump that has a pump inlet and a pump outlet both in fluid communication with inner ear fluid of an implanted patient. The circulation pump is configured to drive the inner ear fluid in from the pump inlet and out through the pump outlet. A pump controller is coupled to the circulation pump and one or more sensing elements for measurement of one or more fluid conditions within the inner ear of the implanted patient, and is configured to control operation of the circulation pump as a function of the measured one or more fluid conditions. Also disclosed is a cochlear implant arrangement and a vestibular implant arrangement comprising such a fluid circulation system.

20 Claims, 5 Drawing Sheets

(56) References Cited

U.S. PATENT DOCUMENTS

| | | | |
|---|---|---|---|
| 5,746,725 A | 5/1998 | Shalon et al. | |
| 2004/0199214 A1 | 10/2004 | Merfeld et al. | |
| 2006/0030837 A1* | 2/2006 | McKenna | A61F 11/00 604/890.1 |
| 2007/0255237 A1 | 11/2007 | Lobl et al. | |
| 2009/0209945 A1* | 8/2009 | Lobl | A61M 5/14224 604/891.1 |
| 2010/0032355 A1 | 2/2010 | Andrews et al. | |
| 2011/0077579 A1 | 3/2011 | Harrison et al. | |
| 2013/0184804 A1 | 7/2013 | Dalton | |
| 2014/0018736 A1* | 1/2014 | Hessler | A61M 5/14276 604/151 |

OTHER PUBLICATIONS

European Patent Office, Extended European Search Report, Application No. 16812272.9, dated Dec. 21, 2018, 7 pages.
China National Intellectual Property Administration, Notification of First Office Action, Application No. 201680035118.5, dated Apr. 24, 2019, with English translation, 15 pages.

\* cited by examiner

APPARATUS FOR TREATMENT OF MENIÈRE'S DISEASE

This application is a national phase entry of Patent Cooperation Treaty Application PCT/US2016/037488, filed Jun. 15, 2016, which in turn claims priority from U.S. Provisional Patent Application 62/181,315, filed Jun. 18, 2015, both of which are incorporated herein by reference in their entireties.

TECHNICAL FIELD

The present invention relates to medical implant systems, and specifically a system to relieve symptoms of Menière's disease and diseases with symptoms similar to Menière's disease.

BACKGROUND ART

Figure 1:
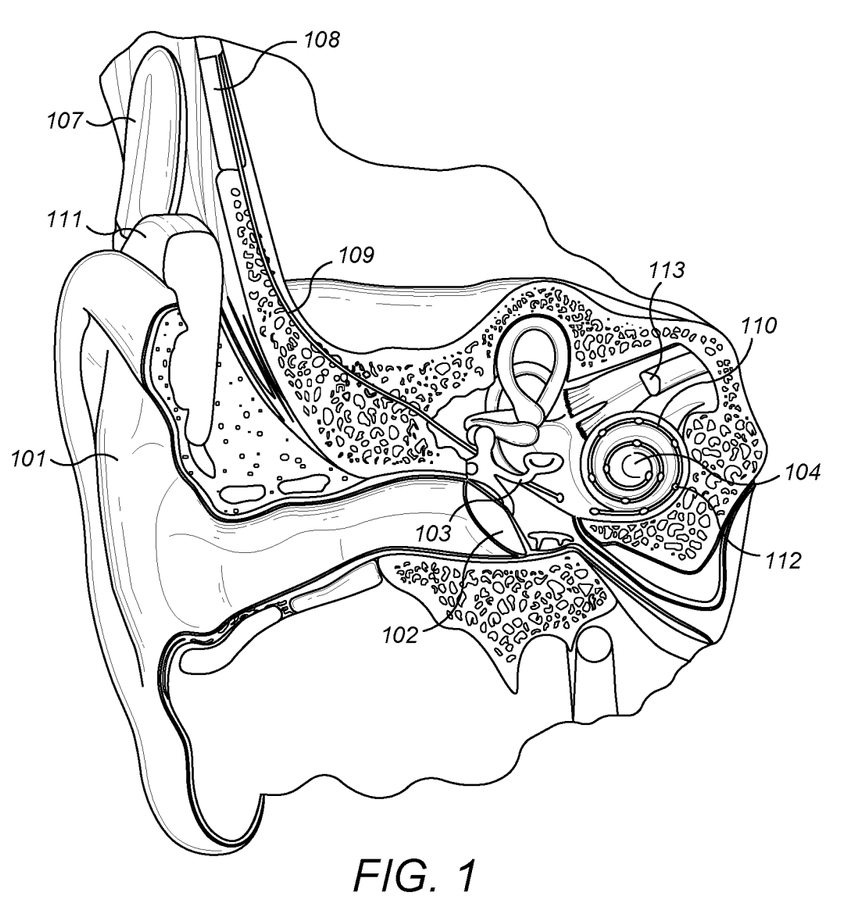
FIG. 1 shows the anatomy of the human ear with a cochlear implant system.

A normal ear transmits sounds as shown in FIG. 1 through the outer ear 101 to the tympanic membrane 102, which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by a central cochlear duct. The cochlea 104 forms an upright spiraling cone with a center called the modiolar where the spiral ganglion cells of the auditory nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. When the impairment is associated with the cochlea 104, a cochlear implant with an implanted electrode can electrically stimulate auditory nerve tissue with small currents delivered by multiple electrode contacts distributed along the electrode.

FIG. 1 also shows some components of a typical cochlear implant system where an external microphone provides an audio signal input to an external signal processor 111 in which various signal processing schemes can be implemented. The processed signal is then converted into a digital data format for transmission by external transmitter coil 107 into the implant device 108. Besides receiving the processed audio information, the implant device 108 also performs additional signal processing such as error correction, pulse formation, etc., and produces an electrical stimulation pattern (based on the extracted audio information) that is sent through an electrode lead 109 to an implanted electrode array 110. The electrode array 110 includes multiple electrode contacts 112 on its outer surface that provide selective stimulation of the adjacent neural tissues within the cochlea 104.

Figure 2:
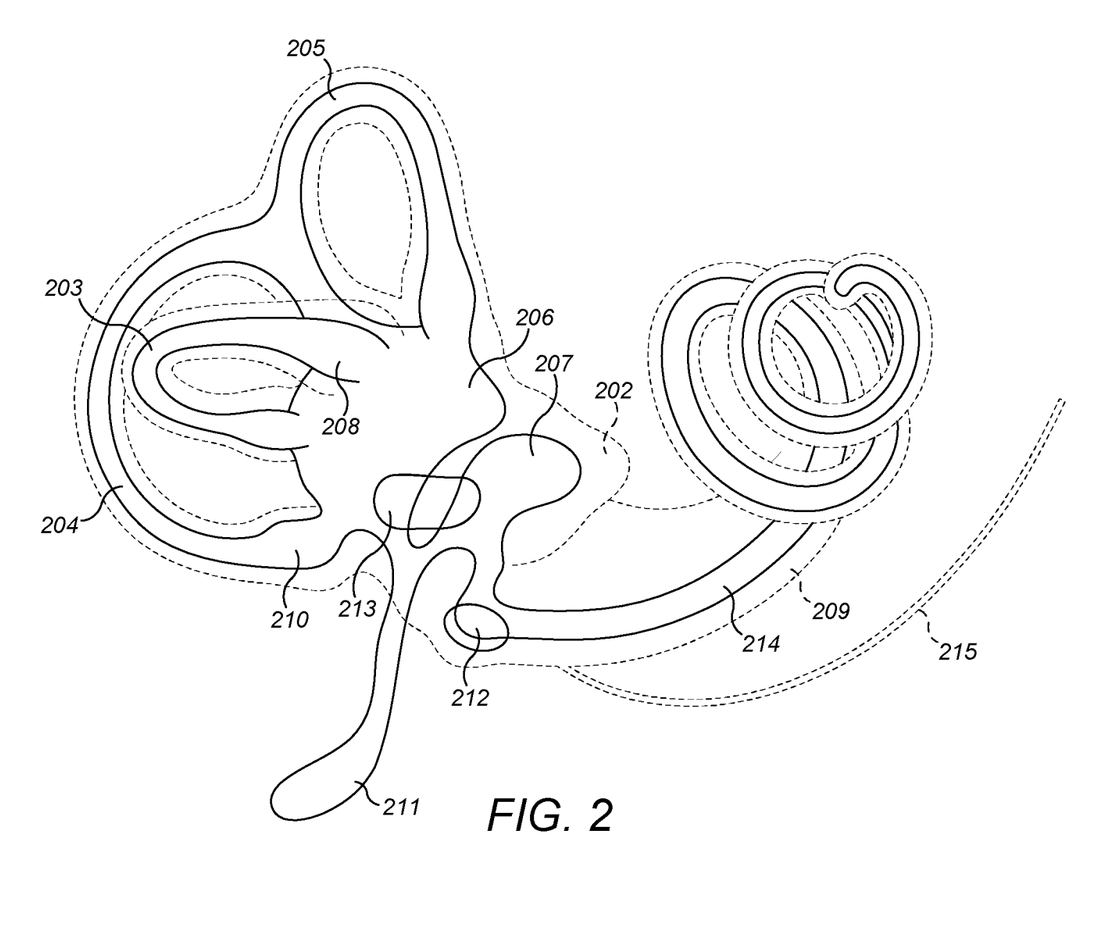
FIG. 2 shows the vestibular system and the fluid compartments with their places of fluid generation and exchange of the inner ear.

Besides developing hearing sensation, the inner ear also provides balance sensing functionality to the brain based on neural signals from the vestibular structures of the inner ear, one on each lateral side of the body. As shown in FIG. 2, each inner ear 200 comprises the cochlea 201 with the cochlear duct 214 and the vestibular system 215. The vestibular system 215 includes five sensing organs: the ampullae 208 of the three semi-circular canals—the horizontal (lateral) canal 203, the posterior canal 204, and the superior canal 205—which sense rotational movement, and the utricle 206 and the saccule 207 in the vestibule 202, which sense linear movement. Further shown are the oval window 213 and round window 212.

The inner volumes of the inner ear are formed by the interconnected cochlea 201 and vestibular system 215 and are divided into two different interior compartments: the endolymph compartment 210 filled with endolymph fluid and the perilymph compartment 209 filled with perilymph fluid. There are several places within the inner ear, in particular within the vestibular system, where endolymph fluid is generated, for example, in the endolymphatic sac 211. Generation of endolymph fluid involves transformation of cranial fluid into endolymph fluid. Similarly, there also is transfer of endolymph fluid to perilymph fluid at certain locations (e.g. along the Reissner's membrane and/or basilar membrane) as well as transfer of perilymph to cranial fluid in both the vestibular and the cochlear system of the inner ear at certain locations (e.g. in the perilymphatic duct 215). It is also assumed that the reverse processes take place. It also is well known that the endolymph fluid in the vestibular system is in fluid communication with that of the cochlear system, and the same applies for the perilymph fluid.

All those different types of inner ear fluid transfer together with the flow channels of the different types of fluids within the inner ear give rise to a slow but continuous circulation of endolymph and perilymph within the inner ear and vestibular system. Typical fluid circulation flow rates may vary over quite a large range from as little as 0.1 µm/s up to hundreds of µm/s to mm/s, varying from patient to patient and strongly depending on the patient's age. Although fluid circulation flow rates vary over a large range, the fluid circulation flow rates for a specific patient normally remains relatively stable and may deviate only during abnormal periods, such as e.g. during Menière disease attacks.

The inner ear and vestibular system can suffer from various disorders that include Menière's disease and autoimmune disease. The attacks that occur with Menière's disease are characterized by various distressing symptoms that can include tremendous dizziness, tinnitus (a continuous ringing perception), and eventually, over time, loss of natural hearing ability. The physiological origins of Menière's disease are not yet fully understood, but in part there is increased pressure in the endolymph.

Menière's disease, tinnitus vertigo, and aural pressure all may be adversely influenced by excess pressure within the inner ear. Such excess pressure may be a consequence of improper fluid circulation within the inner ear. The Meniett device from Medtronic is intended to treat Menière's disease by releasing low frequency pressure waves through the outer ear and the middle ear into the inner ear to influence the pressure in the inner ear. US 2009/0209945 and US2010/0032355 describe apparatuses for treatment of Menière's disease, but neither reference discusses controlled fluid circulation within the inner ear.

SUMMARY

Embodiments of the present invention are directed to an inner ear fluid circulation system. An implantable circulation pump has a pump inlet and a pump outlet both in direct fluid communication with inner ear fluid of an implanted patient. The circulation pump is configured to drive the inner ear fluid in from the pump inlet and out through the pump outlet. A pump controller is coupled to the circulation pump and one or more sensing elements for measurement of one or more fluid conditions and wherein the pump controller configured to control operation of the circulation pump as a function of one or more fluid conditions within the inner ear of the implanted patient.

In further specific embodiments, there may also be a fluid pressure sensor as sensing element that is configured to sense pressure of the inner ear fluid and provide a fluid pressure signal to the pump controller, and the pump controller then controls the operation of the circulation pump as a function of the fluid pressure signal. In addition or alternatively, there may be a fluid flow rate sensor as sensing element that is configured to sense flow rate of the inner ear fluid and provide a flow rate signal to the pump controller; and the pump controller then controls the operation of the circulation pump as a function of the flow rate signal.

The pump inlet and the pump outlet may be located within a cochlea of the implanted patient; for example, on an outer surface of a cochlear or vestibular implant electrode array implanted in the cochlea or vestibular system of the implanted patient as part of a cochlear or vestibular implant. The circulation pump may then be located within the cochlear or vestibular implant electrode array within the cochlea or vestibular system of the implanted patient, or it may be located outside the cochlea or vestibular system of the implanted patient. Alternatively, the pump inlet and the pump outlet may be located within a vestibular system of the implanted patient; for example, in the endolymphatic sac or vestibule of the vestibular system.

In specific embodiments, the circulation pump may be a valveless diffuser/nozzle pump and/or a piezoelectric pump. And the inner ear fluid may be endolymph fluid or perilymph fluid.

DETAILED DESCRIPTION

Embodiments of the present invention are directed to providing relief from the symptoms similar to Menière's disease by reinstating/maintaining circulation of fluid within the inner ear. The invention may therefore provide relief from the symptoms of Menière's disease and autoimmune diseases with or without attacks showing symptoms similar to Menière's disease. An implantable circulation pump is operated to drive the fluid within the inner ear system, preferably such that the targeted flow rate of the endolymph/perilymph to match preoperatively determined target values. The fluid flow within the inner ear or vestibular system enhances or restores transfer of endolymph, perilymph and cranial fluid at the locations as described before for FIG. 2. No fluid leaves the inner ear system and no other fluids or agents enter the system.

Figure 3:
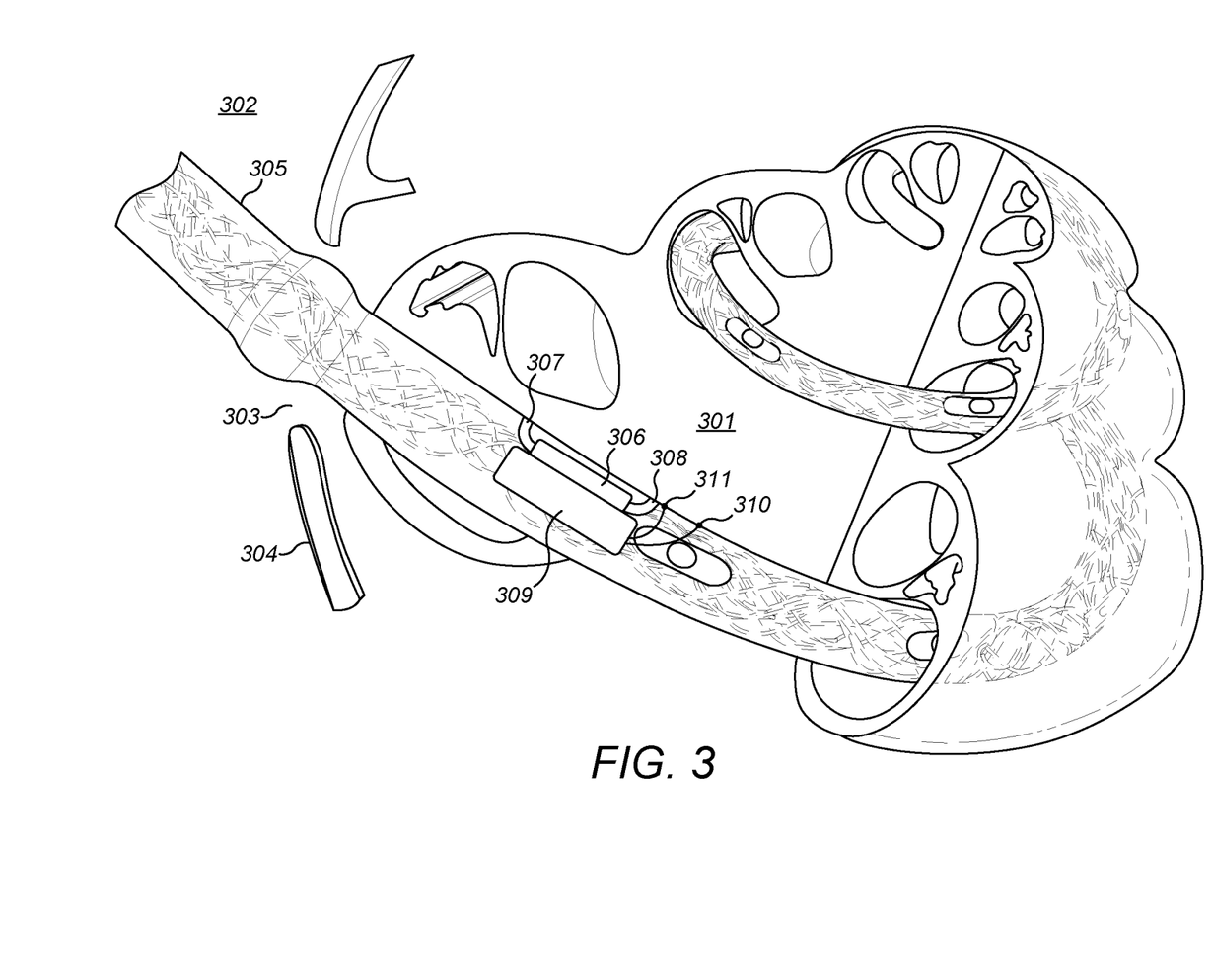
FIG. 3 shows an arrangement for circulation of inner ear fluid according to one embodiment of the present invention.

FIG. 3 shows an arrangement for circulation of inner ear fluid for patients suffering from Menière's disease. An implantable circulation pump 306 is located within a cochlear implant electrode array 305 that is implanted within a cochlea 301 of a recipient patient. Specifically, the outer surface 304 of the cochlea 301 has an electrode insertion opening 303 that is accessible from the middle ear 302 of the patient, through which the electrode array 305 is surgically inserted into the interior of the cochlea 301 so that electrode contacts on the outer surface of the inserted portion of the electrode array 305 can deliver electrical stimulation signals to nearby neural tissue for perception as sound.

The circulation pump 306 has a pump inlet 307 and a pump outlet 308 which end in small openings on the outer surface of the electrode array 305 within the cochlea 301. The pump inlet 307 and the pump outlet 308 are both in direct fluid communication with the fluid in the cochlea 301 (inner ear). The circulation pump 306 is configured to drive the inner ear fluid (which may specifically be endolymph fluid or perilymph fluid) in from the pump inlet 307 and out through the pump outlet 308 to effectuate fluid flow within the inner ear. A pump controller 309 is coupled to the circulation pump 306 and configured to control the operation of the circulation pump 306 based on measurements from one or more sensing elements that measure one or more fluid conditions within the cochlea 301.

The pump inlet 307 and pump outlet 308 may be formed as channels that lead from the embedded circulation pump 306 to small openings on the outer surface of the electrode array 305. Similarly the pressure sensor 310 and/or fluid flow rate sensor 311 may be located form-fit on the outer surface of the electrode array 305. The openings of the pump inlet 307 and pump outlet 308 may be located so as to optimize the fluid flow rate of the inner ear fluid. The pump inlet 307 and pump outlet 308 may be separated along the length of the electrode array 305, for example on the side/opposite side of the electrode contacts. In another example (not shown), the pump inlet 307 and pump outlet 308 may be on opposing sides of the electrode array 305. The pump inlet 307 and pump outlet 308 may form a nozzle to direct the fluid flow into/from a particular direction; for example, perpendicular to/from the outer surface of the electrode array 305. This helps achieve maximum inner ear fluid flow and allows directing the fluid flow into specific regions within the inner ear where fluid-exchange takes place to effectively enhance the fluid-exchange.

Specifically, the circulation pump 306 may be a valveless diffuser/nozzle fluid pump like that described in F. M. White, "Fluid Mechanics", McGraw Hill Book Company, 1986; or in E. Stemme, G. Stemme, "A valveless diffuser/nozzle bases fluid pump", Sens. Actuators A 39 (1993), pp. 159-176). Such a circulation pump 306 may be implanted for chronic treatment and due to the valveless design avoids growth of biological tissue.

Figure 4A:
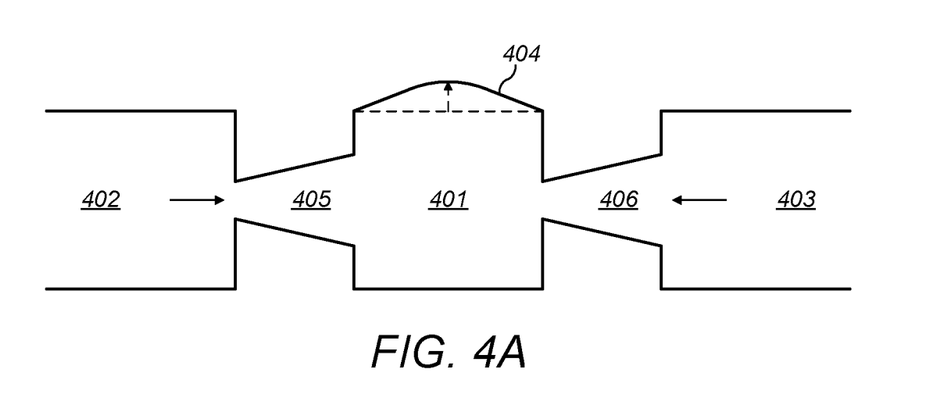
FIGS. 4A-4B show the principle of operation of a valveless diffuser/nozzle pump suitable for use in embodiments of the present invention.
Figure 4B:
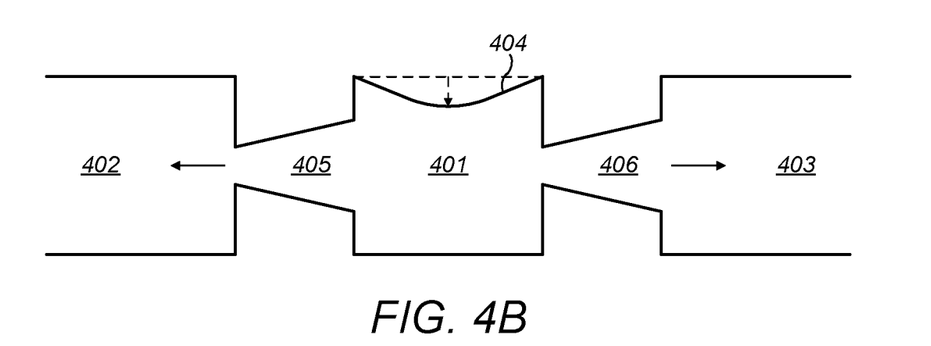

FIGS. 4A-4B show the principle of operation of such a valveless diffuser/nozzle pump. In the intake mode shown in FIG. 4A, a pump diaphragm 404 moves up, increasing the volume of and reducing the pressure in pump chamber 401. The resulting pressure difference between the pump chamber 401 and the pump inlet 402 the pump outlet 403 draws fluid into the pump chamber 401 from both the pump inlet 405 and the pump outlet 406. In this configuration, inlet fluid enters 402 the pump chamber 401 from the pump inlet 405 in a diffuser configuration direction (the heavy arrow), while at the pump outlet 406, outlet fluid 403 enters the pump outlet 406 in a nozzle direction instead (the light arrow). Thus more fluid enters the pump chamber 401 from the pump inlet 405. In the pumping mode shown in FIG. 4B, the reverse process occurs. In a specific embodiment, the pump diaphragm 404 may be actuated with a piezoelectric element such as a piezoelectric membrane or a piezoelectric pump.

A fluid pressure sensor 310 may for example be used as sensing element and is configured to sense pressure of the inner ear fluid in the cochlea 301 and provide a fluid pressure signal to the pump controller 309, and the pump controller 309 then can control the operation of the circulation pump 306 as a function of the fluid pressure signal. There may be in addition or instead of the fluid pressure sensor 310 as sensing element be a fluid flow rate sensor 311 located for example near the pump outlet 308 and configured to sense flow rate of the inner ear fluid and provide a flow rate signal to the pump controller 309. The pump controller 309 may control the operation of the circulation pump 306 as a function of the flow rate signal. The pump controller 309 may control the circulation pump 306 as a function of both the pressure signal and the flow rate signal. The pump controller 309 controls the operating pump flow rate, such as for example the operating frequency of the circulation pump diaphragm 404, to be comparable to the natural circulation flow rate of the inner ear fluid, which may be for example determined preoperatively for a specific patient. Specifically, the pump controller 309 controls the operating pump flow rate of the circulation pump 306 so that the flow rate of the inner ear fluid is in a range from below the natural circulation flow rate, up to about one decade greater than the natural circulation flow rate. For example the pump flow rate may be controlled based at least in part on the measured flow rate signal from the fluid flow rate sensor 311. For example, if the fluid pressure sensor 310 measures a fluid pressure greater than some predetermined threshold pressure and/or the fluid flow rate sensor 311 measures a flow rate less than some predetermined threshold flow rate, the pump controller 309 then causes the circulation pump 306 to start operating to drive the inner ear fluid. It is understood, that the sensing elements may be located at any suitable position during surgery without departing from the invention. For example, the pressure sensor 310 or flow rate sensor 311 may easily be located during surgery easy at a remote, safe and accessible location within the inner ear.

Figure 5:
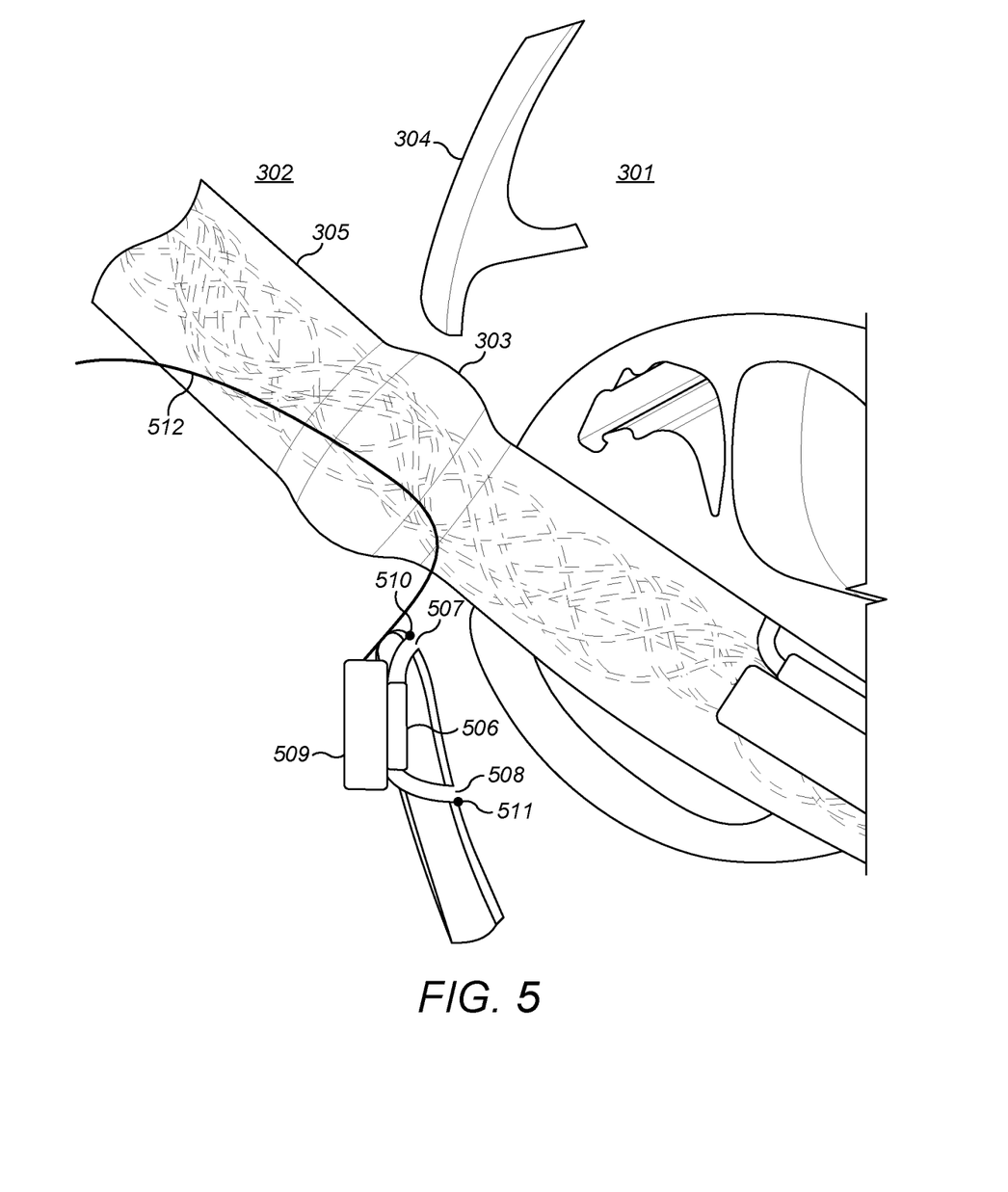
FIG. 5 shows another arrangement for circulation of inner ear fluid according to another embodiment of the present invention.

FIG. 5 shows another arrangement for circulation of inner ear fluid according to another embodiment of the present invention where the circulation pump 506 and the pump controller 509 are located outside the cochlea 301 on the bony outer surface 304. A power supply wire 512 for example within the electrode lead provides electrical power to the circulation pump 506 and the pump controller 509. One tunnel though the outer surface 304 provides access to the interior of the cochlea 301 for a pump intake 507 and fluid pressure sensor 510, and another tunnel through the outer surface 304 provides access to the interior of the cochlea 301 for a pump outlet 508 and fluid flow rate sensor 511. In other embodiments, there may be a single tunnel through the outer surface 304 that provides access to the interior of the cochlea 301.

In another embodiment of the present invention, an arrangement of the circulation pump, the pump controller, pump inlet, and pump outlet may be located in the endolymphatic sac 211 of the vestibular system 215. This placement location may be advantageous since the endolymphatic sac 211 is a primary source for creation of endolymph fluid. The vestibular system 215 also contains a volume of perilymph fluid, and in fact, measurement data suggests that a greater volume of perilymph is concentrated in the vestibular system 215 than is present in the cochlea. The vestibular system 215 also contains the perilymphatic duct, an exchange channel of the perilymph and cerebrospinal fluid, so a circulation pump arrangement may be more effective in the vestibular system 215 and it may be easier to affect or change the course of the amount of the inner ear fluid. Having the circulation pump arrangement placed further from the cochlea also may decrease the prevalence of perceiving unwanted low frequency sounds when the circulation pump operates.

An arrangement for circulation of inner ear fluid may also be useful for patients with symptoms of Menière's disease without hearing loss significant enough to warrant a hearing implant. Such an arrangement might usefully be a modular system that later could support/cooperate with a hearing implant that might be implanted in the future if hearing loss progresses. A modular inner ear fluid circulation pump could include a multi-pin connector configured to provide a later connection for a cochlear implant electrode. A protective cap could initially cover and protect the electrical pins of the multi-pin connector from contact with body fluids. The connector and protective cap can be stored between the first and second operation in an enlarged middle ear space or in an artificially created cavity of the mastoid.

Alternatively, a modular inner ear fluid circulation pump system can be implanted in a first surgery, wherein the electrical connection to the circulation pump and its cooperating sensors is provided by a detachable connector. Then during a second surgery, in the system can be upgraded by a cochlear implant functionality, and the circulation pump and its sensors may be disconnected from the controller (located in an implant pump housing). The original pump housing may be explanted and replaced by a new implant system housing that is connected to the detachable connector. The new implant housing may be attached to a cochlear implant electrode and may further include electrical circuitry within the housing for driving both the inner ear circulation pump and the current to the electrode contacts of the implanted electrode lead.

Although various exemplary embodiments of the invention have been disclosed, it should be apparent to those skilled in the art that various changes and modifications can be made which will achieve some of the advantages of the invention without departing from the true scope of the invention.

What is claimed is:

1. An inner ear implant system comprising:
   an inner ear electrode array with electrode contacts configured to be implanted into a cochlea or into a vestibular system; and
   an inner ear fluid circulation system comprising:
      an implantable circulation pump having a pump inlet and a pump outlet located on an outer surface of the electrode array, the pump inlet and the pump outlet configured to be in fluid communication with inner ear fluid of an implanted patient, and configured to drive the inner ear fluid in from the pump inlet and out through the pump outlet so that no fluid leaves and no other fluids and/or agents enter the inner ear system and wherein the pump inlet and the pump outlet are arranged to effectuate inner ear fluid flow within the inner ear system;
      one or more sensing elements configured to measure one or more fluid conditions within the inner ear of the implanted patient; and
      a pump controller coupled to the circulation pump and the one or more sensing elements, the pump controller configured to control operation of the circulation pump as a function of the measured one or more fluid conditions.

2. The system according to claim 1, wherein the one or more sensing elements includes a fluid pressure sensor configured to sense pressure of the inner ear fluid and provide a fluid pressure signal to the pump controller; wherein the pump controller controls the operation of the circulation pump as a function of the fluid pressure signal.

3. The system according to claim 1, wherein the one or more sensing elements includes a fluid flow rate sensor configured to sense flow rate of the inner ear fluid and provide a flow rate signal to the pump controller; wherein the pump controller controls the operation of the circulation pump as a function of the flow rate signal.

4. The system according to claim 1, wherein the pump inlet and the pump outlet are configured to be located within the cochlea of the implanted patient.

5. The system according to claim 1, wherein the pump inlet and the pump outlet are configured to be located within a vestibular system of the implanted patient.

6. The system according to claim 5, wherein the pump inlet and pump outlet are configured to be located in an endolymphatic sac of the vestibular system.

7. The system according to claim 5, wherein the pump inlet and pump outlet are configured to be located in the vestibule of the vestibular system.

8. The system according to claim 1, wherein the circulation pump is a valveless pump.

9. The system according to claim 8, further comprising a piezoelectric element, wherein the circulation pump is actuated with the piezoelectric element.

10. The system according to claim 1, wherein the inner ear electrode array is a cochlear implant electrode array configured to be implantable into the cochlea of the implanted patient.

11. The system according to claim 10, wherein the circulation pump is located within the cochlear implant electrode array.

12. The system according to claim 10, wherein the circulation pump is configured to be located outside the cochlea of the implanted patient.

13. The system according to claim 10, wherein the pump inlet and the pump outlet are formed as channels that lead from the circulation pump to small openings on the outer surface of the electrode array.

14. The system according to claim 1, wherein the inner ear electrode array is a vestibular implant electrode array configured to be implantable into the vestibular system of the implanted patient.

15. The system according to claim 14, wherein the circulation pump is located within the vestibular implant electrode array.

16. The system according to claim 14, wherein the pump inlet and the pump outlet are formed as channels that lead from the circulation pump to small openings on the outer surface of the electrode array.

17. The system according to claim 1, wherein the pump inlet and the pump outlet are separated along the length of the electrode array.

18. The system according to claim 1, wherein the pump inlet and the pump outlet are on opposing sides of the electrode array.

19. The system according to claim 1, wherein the pump inlet and the pump outlet direct the fluid flow into or from a particular direction.

20. The system according to claim 19, wherein the pump outlet directs the fluid flow perpendicular to the outer surface of the electrode array.

* * * * *